United States Patent [19]

Schwartz et al.

[11] Patent Number: 5,792,103
[45] Date of Patent: Aug. 11, 1998

[54] VISCOSURGICAL METHOD AND APPARATUS

[76] Inventors: Daniel M. Schwartz, 42 Calhoun Terr., San Francisco, Calif. 94133; David G. Hwang, 60 Parkridge Dr., #9, San Francisco, Calif. 94131; Robert Stern, 598 Belvedere, San Francisco, Calif. 94117

[21] Appl. No.: 620,384

[22] Filed: Mar. 22, 1996

Related U.S. Application Data

[63] Continuation-in-part of Ser. No. 383,193, Feb. 3, 1995, abandoned.

[51] Int. Cl.$^6$ .................................................. A61M 37/00
[52] U.S. Cl. ........................... 604/82; 604/51; 128/898; 623/4; 606/107; 424/427
[58] Field of Search ........................ 604/187, 791, 604/49, 51, 56, 27–28; 602/82–85; 606/107; 623/4, 6; 424/427; 128/898

[56] References Cited

U.S. PATENT DOCUMENTS

| | | | |
|---|---|---|---|
| 3,986,510 | 10/1976 | Higuchi et al. | 128/260 |
| 4,173,226 | 11/1979 | Shell | 128/233 |
| 4,328,803 | 5/1982 | Pape | 128/276 |
| 4,713,446 | 12/1987 | Devore et al. | 530/356 |
| 4,851,513 | 7/1989 | Devore et al. | 530/356 |
| 4,923,699 | 5/1990 | Kaufman | 424/427 |
| 5,036,056 | 7/1991 | Kludas | 514/54 |
| 5,066,276 | 11/1991 | Wang | 604/51 |
| 5,166,331 | 11/1992 | Della Valle et al. | 536/55.1 |
| 5,328,462 | 7/1994 | Fischer | 604/82 |
| 5,372,586 | 12/1994 | Haber et al. | 604/89 |
| 5,582,596 | 12/1996 | Fukunaga et al. | 604/191 |
| 5,631,243 | 5/1997 | Kelman et al. | 514/56 |

OTHER PUBLICATIONS

Hawley's Condensed Chemical Dictionary, 12th edition, 1993.
The Merck Index: An Encyclopedia of Chemicals, Drugs, and Biologicals, 10th edition, 1983.
Calder et al., "Hyaluronidase and Sodium Hyaluronate in Cataract Surgery", British Journal of Ophthamology, vol. 70, pp. 418–420, 1986.
Beatrice et al., "Effects of Chronic Intra cameral Injections of Chondroitin Sulfate", Graef's Archive for Clinical and Experimental Ophthamology, vol. 222(1), pp. 1–8, 1984.
Sawaguchi et al., "Effects of Intra cameral Injection of Chondroitinase ABC in Vivo", Archives of Ophthamology, vol. 110 (8), pp. 110–117, 1992.

*Primary Examiner*—Michael Powell Buiz
*Assistant Examiner*—Chalin Smith
*Attorney, Agent, or Firm*—John P. Sutton

[57] ABSTRACT

An improved viscosurgical method involving the administration of a viscoelastic and a corresponding degradative agent, such that the post-operative intraocular pressure spike often observed following the use of viscoelastics in ophthalmic surgery is minimized, and an apparatus and clinical kit useful in the method are provided.

14 Claims, 1 Drawing Sheet

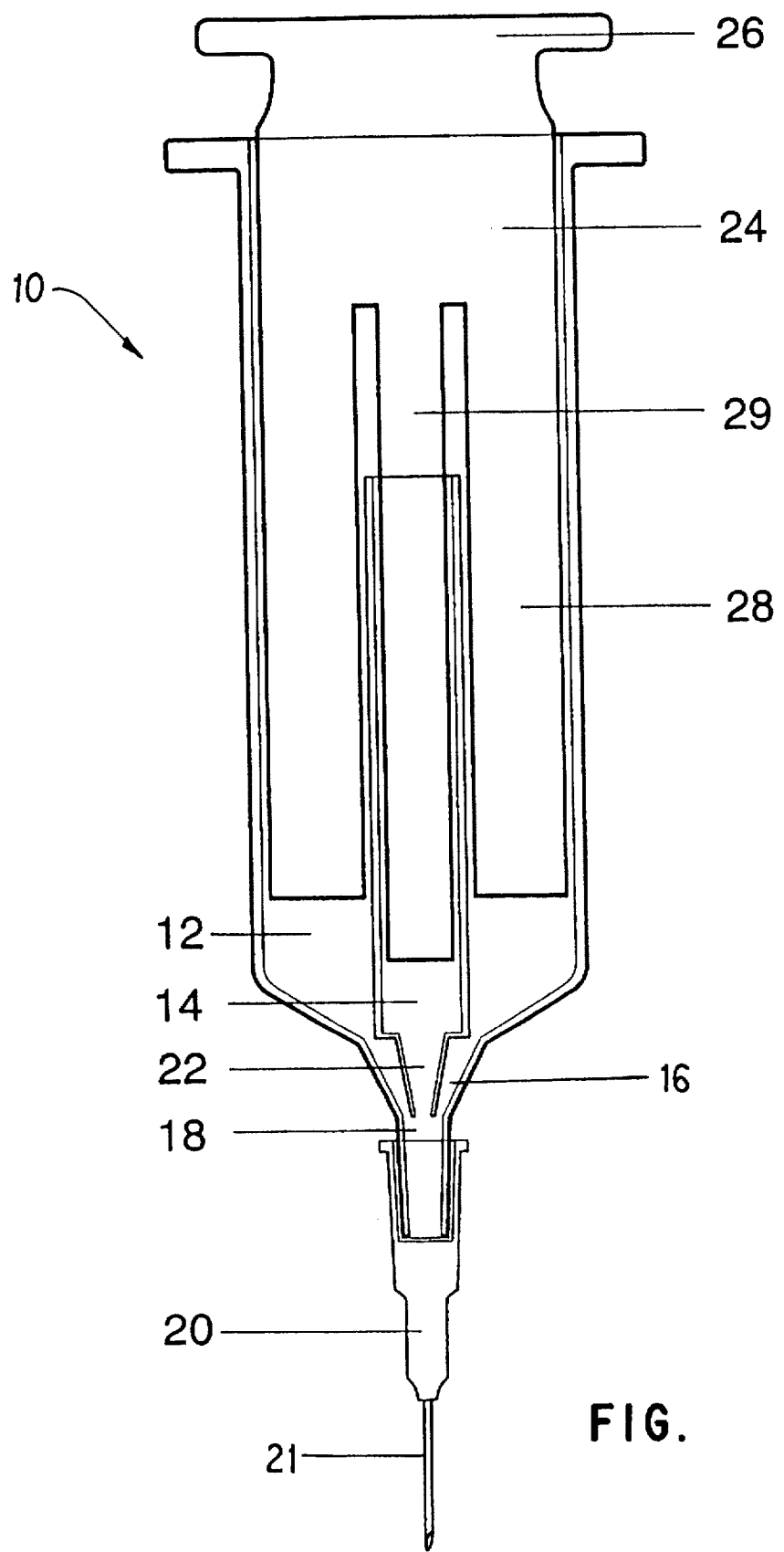

VISCOSURGICAL METHOD AND APPARATUS

This is a Continuation-In-Part of application Ser. No. 08/383,193 filed on Feb. 3, 1995 now abandoned.

The present invention is directed to the use of viscoelastics in ophthalmic surgery, and in particular, to the minimization of the post-operative intraocular pressure spike often observed following viscosurgery. This application is a continuation-in-part of application Ser. No. 08/383,193, filed Feb. 3, 1995.

BACKGROUND OF THE INVENTION

The term viscosurgery refers to the use of viscoelastic substances in intraocular surgery. See Thomas J. Liesegang, *Viscoelastics*, 33(4) Int'l. Ophthalmology Clinics 127 (1993); Rhondi S. Larson et al., *Viscoelastic Agents*, 15(2) Contact Lens Assoc. of Ophthalmologists J. 151 (1989). Viscosurgical methods are frequently used in a variety of ophthalmic surgical procedures including cataract surgery, cornea surgery, glaucoma surgery, vitreous surgery, trauma surgery, intraocular lens implantation, retinal detachment repair, and others. During viscosurgery, a viscoelastic substance may be used as a fluid or as a soft surgical instrument. Some of the tasks performed by viscoelastics include the coating of surfaces, creation of spaces, separation of tissues, displacement of mobile tissue, blocking of the outflow of ocular fluids, confinement of bleeding, exclusion of inflammatory materials, and dampening of the movements of instruments in the eye.

Viscoelastics are solutions that have viscous, elastic, and pseudoplastic properties. They are also characterized by their degree of cohesiveness and coatability. Viscoelastics have dual properties, acting both as viscous liquids and as elastic solids or gels. Liesegang, op. cit., which is incorporated by reference herein, provides a review of viscoelastics used in ophthalmic surgery.

Table 1 provides a brief synopsis of some viscoelastic agents commonly used in ophthalmic surgery together with their commercial and natural sources and selected chemical properties.

Other materials have been used or proposed including high molecular weight carboxymethylcellulose; hydroxypropylcellulose, hydroxyethylcellulose, methylcellulose and mixtures thereof, in combination with polyethylene oxide; carboxyvinyl polymer; polyvinylalcohol; dextran; kitin; and polyvinylpyrrolidone. See U.S. Pat. Nos. 4,965,253 to Goldberg et al., 4,983,585 and 5,156,839 to Pennell et al., 5,204,331 to Nishi et al., and 5,273,056 to McLaughlin.

The most commonly used viscoelastic in ophthalmic surgery is sodium hyaluronate, sold under the trademark Healon®, a registered trademark of Pharmacia Inc., Piscataway, N.J. Healon® is a 1% sodium hyaluronate solution made from the dermis of rooster combs, with a molecular weight of approximately 4 million daltons. Healon® GV (greater viscosity) is also produced by Pharmacia from the dermis of rooster combs and has a concentration of 1.4% and a molecular weight of 5 million daltons. Healon Yellow, with a sodium fluorescein stain (0.005 mg/ml) added to 1% Healon, is available as well. While sodium hyaluronate is currently generally recognized as having the best physical and chemical characteristics for most viscosurgical applications, like all viscoelastics, its use has been associated with a transient increase in intraocular pressure postoperatively.

It is usually desirable to remove all the viscoelastic from the eye at the completion of the surgical procedure. Removal is generally accomplished by irrigation and aspiration. However, since it is usually not possible to remove all of the viscoelastic material by these methods, a residual amount generally remains. Residual viscoelastic must exit through the trabecular meshwork, which is the outlet for aqueous humor egress. It is believed that residual viscoelastic causes obstruction of the trabecular meshwork which is responsible for the post-operative intraocular pressure spike frequently observed following viscosurgery. See Frank G. Berson et al., *Obstruction of Aqueous Outflow by Sodium Hyaluronate in Enucleated Human Eyes*, 95 Am. J. Ophthalmology 668 (1983); Eskil Olivius et al., *Intraocular pressure after cataract surgery with Healon®*, 11 Am. Intraocular Implant Soc. J. 480 (1985). Such an increase in intraocular pressure is cause for concern since it may result in damage to ocular tissues, including the optic nerve (glaucoma).

TABLE 1

Chemical Properties of Viscoelastic Substances

| Solution | Manufacturer | Source | Chemical Compound | Osmolality (mOsm/liter) | Concentration (mg/ml) | Average Molecular Weight (daltons) |
|---|---|---|---|---|---|---|
| Healon ® | Pharmacia | Rooster Combs | Hyaluronic Acid | 302 | 10 | 4,000,000 |
| Healon ® GV | Pharmacia | Rooster Combs | Hyaluronic Acid | 310 | 14 | 5,000,000 |
| Amvisc ® | Iolab | Rooster Combs | Hyaluronic Acid | 318 | 10 | 1,000,000 |
| Amvisc ® Plus | Iolab | Rooster Combs | Hyaluronic Acid | 340 | 16 | 2,000,000 |
| Vitrax ® | Allergan | Rooster Combs | Hyaluronic Acid | 310 | 30 | 500,000 |
| Viscoat ® | Alcon | Bacterial Fermentation | Hyaluronic Acid | 325 | 30 | 500,000 |
|  |  | Shark Fin | Chondroitin Sulfate | — | 40 | 25,000 |
| Ocucoat ® | Storz | Wood Pulp | Hydroxypropyl-methylcellulose | 285 | 20 | 86,000 |
| Ocugel ® | Surgidev | Wood Pulp | Hydroxypropyl-methylcellulose | 310 | 27.5 | 100,000 |
|  |  | Shark Fin | Chondroitin Sulfate | — | 5.0 | 25,000 |
| Orcolon ® | Optical Radiation | Synthetic Polymer | Polyacrylamide | 340 | 4.5 | 1,000,000 |
| Collagel ® | Dimilens | Human Placenta | Type IV collagen | 300 | 14 | 1,000,000 |

*Liesegang, op. cit., p. 131

Accordingly, improved viscosurgical techniques are needed in order to reduce or avoid the problem of increased postoperative intraocular pressure.

It has also been shown that irrigation of the anterior and posterior chambers of enucleated eyes with a hyaluronidase, an enzyme that cleaves the glycosidic bonds of hyaluronic acid and its salts, following administration of hyaluronic acid, increases the outflow facility of enucleated eyes relative to irrigation without a hyaluronidase. See Berson et al., op. cit.; Barany et al., *Influence of Testicular Hyaluronidase on the Resistance to Flow through the Angle of the Anterior Chamber,* 30 Acta Phys. Scandinav. 240 (1953). A trial of hyaluronidase injection after hyaluronic acid installation during cataract surgery on ten patients showed a lowering of the pressure spike in Calder et al. Hyaluronidase and Sodium Hyaluronate in Cataract Surgery, 70 British J. of Ophthalmology 418–20 (1986).

Despite lowering the intraocular pressure after hyaluronic acid installation, sequential injection of viscoelastic and degradative agent is problematic. If a small volume of concentrated degradative agent is injected at the end of the procedure, there is a risk that pockets of highly concentrated degradative agent will accumulate at the point of injection, with risk of damage to tissue. If the degradative agent is held near the corneal endothelium by the viscoelastic agent, the degradative agent could damage this fragile cellular layer. Further, if accidental intracorneal injection of the concentrated degradative agent were to occur this could opacify the transparent cornea and even induce irregular changes in refractive error. Another problem with sequential injection of viscoelastic followed by degradative agent would be in the gas filled eye during vitrectomy procedures. In the gas filled eye, viscoelastic is sometimes used to coat the corneal endothelium as a means to smooth out Descemet's folds that obscure visualization of the retina. If the degradative agent were injected into the gas filled eye to degrade the viscoelastic, most of the degradative agent would simply fall through the gas onto the surface of the retina, not mixing with the viscoelastic which coats the corneal endothelium. Not only would the sequentially injected degradative agent not mix with the viscoelastic, but once it fell onto the retina, it might be very toxic in its concentrated form. See Gottleib et al., *The Safety of Intravitreal Hyaluronidase,* 31 Investigative Ophtamology and Visual Sci. 2345 (1990).

It has been suggested that hyaluronate may be mixed with hyaluronidase and then injected into the eye as a way to reduce the intraocular pressure spike that occurs with hyaluronic acid injection alone. Stephen R. Hein et al., *Elimination of Sodium Hyaluronate—Induced Decrease in Outflow Facility with Hyaluronidase,* 17 Ophthalmic Surgery 731 (1986). In this reference, the authors do not specify how or when the mixture of hyaluronidase and hyaluronic acid is prepared. If the viscoelastic and degradative agent are mixed in a separate container before injection into the eye, two problems develop. First, bubbles form in the viscous mixture upon stirring. When bubbles are drawn into a syringe and injected into the eye, they are difficult to remove. The surgeon is unable to see through bubbles to perform surgery.

The second problem is that degradation of hyaluronate begins immediately upon contact with hyaluronidase, reducing the viscosity. A delay of even five or ten minutes, a commonplace occurrence in surgery, will lower the viscosity of the mixture to a viscosity level inadequate for the intended use. In addition, viscoelastic is typically needed more than once during a procedure. If a batch is mixed before beginning the procedure, it will be useless when injected near the end of the procedure. There is a need mix the viscoelastic and the degradative agent at the time of injection into the eye, and not before, each time it is needed. Furthermore, the viscoelastic and degradative agent must be kept separate until they are injected to prevent loss of viscosity during the procedure.

It is an object of the present invention to provide an improved method for administration of viscoelastics in ophthalmic surgery that reduces or eliminates post-operative intraocular pressure increases.

It is a further object of the present invention to provide an apparatus useful for administration of viscoelastics according to the improved method of the present invention.

It is another object of the present invention to provide a clinical kit for use of the method and apparatus of the present invention in viscosurgery.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention provides an improved method of use of intraocular viscoelastics which minimizes postoperative intraocular pressure increases. In the method, a physiologically acceptable viscoelastic is administered to the intraocular cavity during surgery. The improvement comprises administering to the intraocular cavity a physiologically acceptable degradative agent for the viscoelastic in a sufficient amount and with sufficient mixing to substantially degrade the viscoelastic thereby minimizing post-operative intraocular pressure increase.

The present invention further provides an improved apparatus for intraocular administration of a viscoelastic. The apparatus comprises a chamber containing the viscoelastic, an outlet leading from said chamber to a passage accessible to the intraocular cavity, and means for forcing the viscoelastic into the intraocular cavity. The improvement comprises a second chamber for a degradative agent for the viscoelastic. The second chamber has an outlet leading to either the same or a different passage accessible to the intraocular cavity, and means, which may be the same means as for the first chamber, for forcing the degradative agent into the intraocular cavity, whereby the degradative agent and viscoelastic are substantially mixed.

The present invention additionally comprises a viscosurgical clinical kit. The kit comprises an apparatus for intraocular administration of a viscoelastic, comprising a chamber containing the viscoelastic, an outlet leading from the chamber to a passage accessible to the intraocular cavity, and means for forcing the viscoelastic into the intraocular cavity. The improvement comprises a second chamber for a degradative agent for the viscoelastic. The second chamber has an outlet leading to either the same or a different passage accessible to the intraocular cavity, and means, which may be the same means as for the first chamber, for forcing the degradative agent into the intraocular cavity, whereby degradative agent and viscoelastic are substantially mixed. The kit additionally comprises a physiologically acceptable, viscoelastic in the first chamber, and a physiologically acceptable degradative agent for the viscoelastic in the second chamber. The agent is capable of substantially degrading the viscoelastic such that post-operative intraocular pressure increases are minimized.

BRIEF DESCRIPTION OF THE DRAWING

The Figure shows a schematic vertical section of an embodiment of the apparatus for administering a viscoelastic agent and degradative agent to the intraocular cavity according to the present invention.

DESCRIPTION OF THE INVENTION

The present invention is directed to an improved viscosurgical method which involves intraocular administration of a viscoelastic in conjunction with a degradative agent for the viscoelastic. Both the viscoelastic and its degradative agent must be physiologically compatible separately and in combination, that is, they must not be harmful to the ocular tissues to which they are exposed. The degradative agent should be administered to the intraocular cavity at or about the same time as the administration of the viscoelastic, providing that thorough mixing with the viscoelastic is achieved so that the viscoelastic is substantially degraded at the appropriate time and post-operative intraocular pressure increases are reduced or eliminated.

The maximum rise in postoperative intraocular pressure generally occurs 4 to 7 hours following viscosurgery, and returns to normal in most patients by 24 hours. See Liesegang, op. cit., p. 145. Accordingly, for many applications, an appropriate degradative agent will begin degrading its corresponding viscoelastic within about from 0 to 4 hours following surgery so that the post-operative intraocular pressure spike is reduced or eliminated. Preferably, sufficient degradation to avoid a detrimental post-operative intraocular pressure increase will be achieved within about 30 to 60 minutes following surgery. The invention is not limited to these time periods, however. Degradation times may be varied as appropriate for a particular individual or procedure.

The normal acceptable range for intraocular pressure is between about 5 to 21 millimeters of mercury (mm Hg), depending on the individual. While the range of normal intraocular pressures may vary between individuals, in general, intraocular pressures of 22 mm Hg or more are cause for concern since such elevated intraocular pressures may cause ocular tissue damage in susceptible individuals, including those with glaucoma. Therefore, while any reduction in the post-operative pressure spike will be of some benefit, degradation should preferably proceed sufficiently rapidly so that this pressure is not reached.

This improved method is applicable in any viscosurgical operation. For some applications, such as in a gas-filled eye, co administration of the viscoelastic and degradative agent will be required. There must be sufficient contact between the viscoelastic and its degradative agent to allow the degradative agent to substantially degrade the viscoelastic so that post-operative intraocular pressure increases are reduced or eliminated without local toxic effects. Mixing is important to prevent accumulation of local pockets of high concentrations of the degradative agent that could inhibit substantial degradation of the viscoelastic and have potentially toxic effects.

Viscoelastics useful in viscosurgery will be known to those skilled in the art. Suitable viscoelastics according to the present invention will generally have the following properties:

(i) Isomolarity with the physiological environment of the eye (osmolarity of about 250–350, buffered to a pH of from about 7.0 to 7.5) for physiological compatibility;

(ii) Gel-like high viscosity at low shear (at least about 5000 centipoises (cps)) to prevent loss by leakage through wound openings and enable gentle tissue manipulation;

(iii) Lubricating and having adequate coatability for protection of corneal endothelium, iris, and other sensitive tissues from contact with instruments or implants;

(iv) Injectable for administration; and (v) Capable of being substantially degraded by an intraocularly administered degradative agent.

In addition, suitable viscoelastics will also generally be optically clear, inert, sterile, nontoxic, nonpyrogenic, noninflammatory, and nonimmunogenic.

The term "degradative agent" as used herein means any physiologically acceptable substance that can degrade an associated viscoelastic to the extent that post-operative intraocular pressure increases are reduced. The term includes substances that act directly on viscoelastics, as well as those whose degradative effect is induced by additional chemical, physical or other means.

Degradative agents according to the present invention may act on their corresponding viscoelastic agents substrates by various mechanisms. These mechanisms include, but are not limited to, enzymatic cleavage of a specific bond in a polymeric substrate, and depolymerization induced by chemical agents, ions, or free radicals.

Examples of suitable viscoelastic agents, and their corresponding degradative agents, which may be used in the method of the present invention are listed in Table 2, below. This list is provided in order to more clearly describe the present invention. However, the invention is not limited to the use of the compounds listed below. Any combination of a viscoelastic and its appropriate corresponding degradative agent or agents which is suitable for a viscosurgical application may be used.

TABLE 2

Viscoelastics And Corresponding Degradative Agents Useful In The Present Invention

| VISCOELASTIC AGENT | DEGRADATIVE AGENT |
|---|---|
| hyaluronate | hyaluronidase |
| hyaluronate | ascorbate |
| hyaluronate | metal ions (Fe++, Cu++) |
| hyaluronate | $Fe^{3+}$; ascorbate |
| hyaluronate | hydrogen peroxide |
| hyaluronate | chondroitinase |
| hyaluronate | cysteine |
| hyaluronate | hypochlorite ion (OCl—) |
| chondroitin sulfate | chondroitinase |
| chondroitin sulfate | hyaluronidase |
| methylcellulose | cellulase |

* Riboflavin and ethylenediaminetetraacetic acid have also been reported to degrade hyaluronate.

The particular administration protocol and amounts of viscoelastic and degradative agent used are selected in accordance with the requirements of the particular surgical procedure. In general, sufficient degradation of the viscoelastic by the degradative agent to reduce the post-operative intraocular pressure spike is required. Preferably, sufficient degradation will be achieved to prevent any detrimental increase in post-operative intraocular pressure. Dosages of degradative agent should be sufficient to achieve this purpose without generating any toxic effects. However, the viscoelastic and degradative agent must be kept separate until they are injected to prevent loss of viscosity during the procedure.

Commercially available degrading agents may not be compatible with safe intraocular administration. For example, Wydase, (Wyeth-Ayerst) a commonly used preparation, has numerous protein impurities noted when it is analyzed by sodium dodecyl sulfate polyacrylamide gel electrophoresis (SDS-PAGE). We have demonstrated significant differences in corneal toxicity following intraocular injection between Wydase and a Sigma preparation of bovine testicular hyaluronidase (Type V1-S/H3631). Because the Sigma preparation has many fewer protein impurities noted on SDS-PAGE, purification of the enzyme may be important in reducing intraocular toxicity. There are two convenient ways to obtain pure enzyme known in the art. One is passing through successive chromatography columns to separate the enzyme from other proteins. The other is to utilize an expression system after cloning the enzyme. Additionally, the accompanying vehicle may be equally or, even more important, in accounting for differences in the intraocular toxicity of different hyaluronidase preparations. The degradative agent used should thus be as pure as possible, mixed with an appropriate vehicle to insure safety following intraocular injection.

The viscoelastic and degradative agent are generally administered to the eye according to the method of the present invention following creation of a surgical opening. A preferred mode of administration is by injection into the chamber or region of the eye appropriate for the particular surgical procedure to be undertaken. The viscoelastic and degradative agent may be administered to the eye according to the present invention using an apparatus specifically designed for the task, or using other delivery means for fluid substances known in the art.

The present invention also provides an apparatus for surgical applications wherein administration of the viscoelastic and degradative agent at or near the same time is desirable or necessary. The apparatus provides mixing and simultaneous or near simultaneous injection of the viscoelastic and its degradative agent.

Referring to the Figure, a preferred embodiment of an apparatus according to the present invention is shown. The apparatus is a specialized syringe 10 having one chamber 12 for containing a viscoelastic, and a second chamber 14 for containing a degradative agent for the viscoelastic. In this embodiment, the second chamber 14 is coaxial within the first chamber 12. However, the two chambers may be organized in any other way that allows for the effective delivery to the eye.

The overall and relative capacities of the chambers 12, 14 are determined by the amount of viscoelastic needed to fill the appropriate chamber or region of the intraocular cavity, and the amount of degradative agent needed to provide the required amount of degradation of the viscoelastic. Factors in this determination include the particular viscoelastic and degradative agent selected, the vehicle for the degradative agent, and the nature of the surgical procedure undertaken. Rather than dissolving the degrading agent in a low viscosity solution such as balanced saline, a different viscoelastic not subject to degradation by the degrading agent may be used in the second chamber, 14. By dissolving the degrading agent in a viscoelastic, the viscosity of the viscoelastic in the first chamber, 12, is largely maintained when the degrading agent is mixed with it from the second chamber at or near the time of intraocular injection. By way of example, Viscoat is a commonly used viscoelastic containing a mixture of chondroitin sulfate and hyaluronic acid. Hyaluronidase derived from Streptomyces may be placed in the second chamber 14, which contains pure chondroitin sulfate. The substrate specific hylauronidase in the second chamber does not dissolve the chondroitin sulfate in the same chamber. At the time of injection the hyaluronic acid, chondroitin sulfate, and hyaluronidase all mix together, similar to mixing hyaluronidase with Viscoat. The hyaluronic acid is digested by the hyaluronidase, thus minimizing the intraocular pressure spike. Capacities in the range of about 0.4 to 1.2 and 0.1 to 0.5 cubic centimeters for the viscoelastic and degradative agent chambers, respectively, will be suitable for many applications.

The apparatus is further provided with an outlet 16 leading from the first chamber 12 to a passage 18 which is designed to provide access to the intraocular cavity. The passage 18 is equipped with a tip 20 having the appropriate size and shape for administration of the viscoelastic and its degradative agent to the intraocular cavity with minimal damage to sensitive ocular tissues. For example, the tip 20 may terminate in a 25 to 30 gauge sharpened needle. Alternatively, the tip may comprise a similarly sized cannula.

The second chamber 14 also has an outlet 22 leading to a passage accessible to the intraocular cavity. In the embodiment shown in the Figure, the second outlet 22 leads to the same passage 18. Alternatively, the second outlet 22 may lead to a separate passage accessible to the intraocular cavity. In the preferred embodiment shown in the figure, mixing of the viscoelastic and the degradative agent occurs, or at least starts, in the passage 18 prior to injection.

The apparatus also has a plunger 24 for forcing the viscoelastic and degradative agent into the intraocular cavity. The plunger 24 has a handle 26 at its proximal end for manipulation, and separate shafts 28, 29 to provide controlled ejection of the agents from their respective chambers 12, 14 into the passage 18.

Syringes according to the present invention are made of materials which are unreactive with the viscoelastic and degradative agent they are to administer. Suitable materials include polypropylene, stainless steel, aluminum, polycarbonate, glass, butyl rubber and epoxy glues. The syringes are fabricated according to procedures known in the art.

Apparatuses according to the present invention are not limited to syringes, but may take other forms which are able to effectively mix and deliver the appropriate amounts of the viscoelastic and degradative agent into the intraocular cavity at or near the same time.

In addition, an apparatus according to the present invention may be pre-loaded with a viscoelastic and corresponding degradative agent to provide a clinical kit for the practice of the method of the present invention.

Following are examples of the method of the present invention in practice. The examples are provided in order to further describe the invention and are not intended to limit its scope.

EXAMPLE 1

Example Of A Viscoelastic And Corresponding Degradative Agents Useful In The Practice Of The Present Invention Sodium hyaluronate is a linear, unbranched, large polysaccharide molecule with a random coil configuration present in nearly all connective tissues of vertebrate organisms. In the eye, it is found in relatively high concentrations in the vitreous, and in lower concentrations in the aqueous humor, connective tissue of the trabecular meshwork, and covering the endothelium. Accordingly, the use of sodium hyaluronate in viscosurgery does not represent introduction of a foreign material.

Various biological sources, including the umbilical cord, bovine vitreous, and rooster comb, contain a large amount of sodium hyaluronate. Production of lower-molecular weight sodium hyaluronate may also be achieved by bacterial synthesis. See S.F. Bernatchez et al., *Use of Hyaluronic acid in ocular therapy.* In Edman, P., ed., *Biopharmacology of ocular drug delivery,* pp. 105–120 (1993). Sodium hyaluronate consists of repeating disaccharide units of N-acetyl-D-glucosamine and glucuronate linked by β1–3 and β1–4 glycoside bonds. It belongs to the glycosaminoglycan group of polysaccharides and contains hexosamine. It does not contain significant covalently bound protein, peptides, amino acids, other sugar molecules, or nucleic acids. There do not appear to be any permanent cross-links between individual chains. The chemical structure is independent of the origin, but the molecular weight varies dramatically depending on the source. See Liesegang, op. cit.

Hyaluronidase, as used herein, is an enzyme composition which randomly cleaves glycosidic bonds of hyaluronic acid. The term "hyaluronidase" is used generically to identify one or more specific enzymes that have this activity in common. "Hyaluronidase" used according to the present invention may be any one or a mixture of such enzymes.

EXAMPLE 2

Application Of The Present Invention In Cataract Surgery

During cataract surgery, viscoelastic is injected into the anterior chamber after it is opened by an incision at or near the limbus. The viscoelastic maintains the anterior chamber and protects the endothelium during anterior capsulotomy. Approximately 0.1–0.3 cc of sodium hyaluronate (Healon®) and hyaluronidase are co-injected into the anterior chamber. After performing the capsulotomy and removal of the cataract, combined viscoelastic and degradative agent are is again used to reform the chamber, and fill the capsular bag for placement of the intraocular lens. A larger volume of viscoelastic is usually injected at this time. Following placement of the intraocular lens, the Healon® mixed with hyaluronidase may be irrigated and aspirated from the eye. Residual Healon® is degraded by the co-administered hyaluronidase.

EXAMPLE 3

Application Of The Present Invention In Vitreous Surgery

During vitreous surgery, after the eye is filled with gas, there are sometimes folds of Descemet's membrane and the corneal endothelium, making it difficult to visualize the fundus for laser photocoagulation or further intraocular maneuvers. Viscoelastic is used to coat the inner surface of the cornea to smooth out these folds and improve visualization of the posterior fundus. In the air-filled eye, the degradative agent and viscoelastic must be administered simultaneously. If the degradative agent were administered after the viscoelastic was used to coat the corneal endothelium, much of the degradative agent would fall onto the retina without degrading the viscoelastic. Approximately 0.1–0.3 cc of sodium hyaluronate (Healon®) and 1–25 USP units of hyaluronidase are injected to coat the corneal endothelium. At the conclusion of the procedure, Healon® may be aspirated from the anterior chamber. Residual Healon®, or all the administered Healon® where there is no aspiration, is degraded by the co-administered hyaluronidase.

EXAMPLE 4

Application Of The Present Invention In Penetrating Keratoplasty

Prior to removal of the host corneal button, a viscoelastic mixture of approximately 0.1–0.3 cc of sodium hyaluronate (Healon®) and hyaluronidase are injected into the anterior chamber to pressurize the eye for trephination. Following removal of the graft, if an intraocular lens is placed, this is also coated with the viscoelastic mixture. At the conclusion of the procedure, the anterior chamber is reformed with saline or additional viscoelastic mixture. Viscoelastic is not ordinarily removed in these cases so that it can maintain the anterior chamber and protect the donor corneal endothelium. This commonly causes elevations of post-operative intraocular pressure which can damage the donor corneal tissue. With the self-degrading viscoelastic mixture of the present invention, however, pressure elevations are minimized with less ensuing damage to the cornea and other intraocular structures.

EXAMPLE 5

Application Of The Present Invention In Vitreous Surgery In Pseudophakic Eye During vitreous surgery in the pseudophakic eye, fluid-gas exchange often causes air to leak around the intraocular lens (IOL) into the anterior chamber. This makes the view of the posterior pole quite difficult. To prevent air from getting into the anterior chamber the vitreous surgeon will administer viscoelastic to the anterior chamber prior to fluid-gas exchange. A viscoelastic mixture of approximately 0.1–0.3 cc of sodium hyaluronate (Healon®) and hyaluronidase is administered by injection. At the conclusion of surgery, the viscoelastic may or may not be aspirated from the anterior chamber. Traditionally aspiration is used to reduce the concentration of the viscoelastic. According to the present invention, aspiration is not always necessary because the degradative agent prevents post-operative pressure spike. A step in the surgical procedure may thus be eliminated in some cases. Residual viscoelastic is degraded by the hyaluronidase so that post-operative elevations of intraocular pressure are avoided.

What is claimed is:

1. In a viscosurgical method, wherein a physiologically acceptable viscoelastic is administered to the intraocular cavity during surgery, the improvement comprising administering to the intraocular cavity a physiologically acceptable degradative agent for the viscoelastic in a sufficient amount and with sufficient mixing at about the time of injection of the viscoelastic to substantially degrade the viscoelastic thereby minimizing post-operative intraocular pressure increase.

2. A method according to claim 1, wherein the degradative agent degrades the viscoelastic prior to a detrimental increase in post-operative intraocular pressure.

3. A method according to claim 1, wherein said viscoelastic is chondroitin sulfate and said degradative agent is chondroitinase.

4. A method according to claim 1, wherein said viscoelastic is methylcellulose and said degradative agent is cellulase.

5. A method according to claim 1, wherein said degradative agent is $Fe^{3+}$ and said inducing agent is ascorbate.

6. A method according to claim 1, wherein said viscoelastic is an aqueous solution of a compound selected from the group consisting of hyaluronic acid, its salts and mixtures thereof, and said degradative agent is selected from the group consisting of hyaluronidase, chondroitinase, ascorbate, metal ions, riboflavin and ethylenediaminetetraacetic acid.

7. A method according to claim 6, wherein said viscoelastic is sodium hyaluronate and said degradative agent is hyaluronidase.

8. A method according to claim 6, wherein said viscoelastic is sodium hyaluronate and said degradative agent is chondroitinase.

9. A method according to claim 6, wherein said viscoelastic is sodium hyaluronate and said degradative agent is ascorbate.

10. A method according to claim 6, wherein said viscoelastic is sodium hyaluronate and said degradative agent is Fe++.

11. A clinical kit for intraocular surgery on a patient comprising a housing having a chamber therein containing a viscoelastic and a chamber in the housing containing a degradative agent for the viscoelastic, each of said chambers having an outlet, and said housing having an outlet in close proximity to the outlets for the chambers, whereby the viscoelastic and degradative agent are mixed at or near the outlet from the housing.

12. A clinical kit as in claim 11, in which the two chambers are coaxial within a syringe housing.

13. A clinical kit as in claim 11, in which the outlet for the viscoelastic chamber and the outlet for the degradative agent chamber are immediately adjacent the outlet for the housing, whereby mixing occurs as the contents of the two chambers emerge from the outlet from the housing.

14. A clinical kit as in claim 11, in which the outlet from the housing feeds a surgical needle for accurately placing the mixture in the eye of the patient.

* * * * *